US012594375B2

(12) United States Patent
Steins

(10) Patent No.: US 12,594,375 B2
(45) Date of Patent: Apr. 7, 2026

(54) SILENT PUMPING MECHANISM FOR INFUSION PUMP

(71) Applicant: CareFusion 303, Inc., San Diego, CA (US)

(72) Inventor: Carsten Steins, Ubach-Palenberg (DE)

(73) Assignee: CareFusion 303, Inc., San Diego, CA (US)

( * ) Notice: Subject to any disclaimer, the term of this patent is extended or adjusted under 35 U.S.C. 154(b) by 930 days.

(21) Appl. No.: 17/605,712

(22) PCT Filed: Apr. 22, 2020

(86) PCT No.: PCT/US2020/029359
§ 371 (c)(1),
(2) Date: Oct. 22, 2021

(87) PCT Pub. No.: WO2020/219574
PCT Pub. Date: Oct. 29, 2020

(65) Prior Publication Data
US 2022/0305197 A1 Sep. 29, 2022

Related U.S. Application Data

(60) Provisional application No. 62/837,529, filed on Apr. 23, 2019.

(51) Int. Cl.
A61M 5/142 (2006.01)
F04B 43/08 (2006.01)

(52) U.S. Cl.
CPC ......... A61M 5/14228 (2013.01); F04B 43/08 (2013.01); A61M 2205/42 (2013.01)

(58) Field of Classification Search
CPC .......... A61M 5/14228; A61M 5/14232; A61M 2205/42; F04B 43/10; F04B 43/12; F04B 43/04; F04B 53/001; F04B 53/003
See application file for complete search history.

(56) References Cited

U.S. PATENT DOCUMENTS 4,155,362 A * 5/1979 Jess .......................... A61M 5/36
604/890.1
4,210,138 A * 7/1980 Jess ................... A61M 5/16804
604/153

(Continued)

FOREIGN PATENT DOCUMENTS

CN 1254296 A 5/2000
CN 103068420 A 4/2013
(Continued)

*Primary Examiner* — Emily L Schmidt
*Assistant Examiner* — Samuel J Marrison
(74) *Attorney, Agent, or Firm* — Mintz Levin Cohn Ferris Glovsky and Popeo, P.C.

(57) ABSTRACT

Features relating to a pumping mechanism of a peristaltic infusion pump are provided. Stabilizing protrusions are provided for one or more pumping fingers of the pumping mechanism, where the one or more pumping fingers move in a coordinated and synchronized fashion with respect to one another to provide a controlled peristaltic action against a flexible tube for delivery of a fluid to a patient. The protrusions extend outward from one or more side regions of the pumping fingers to create points of contact on a side-wall of a recess in a chassis in which the pumping mechanism is positioned. The points of contact serve to stabilize the fingers to prevent vibration and/or movement of the fingers against the sidewall.

16 Claims, 9 Drawing Sheets

(56) References Cited

U.S. PATENT DOCUMENTS

| | | | |
|---|---|---|---|
| 4,394,862 A * | 7/1983 | Shim ................. | A61M 5/16854 |
| | | | 128/DIG. 13 |
| 4,725,205 A | 2/1988 | Cannon et al. | |
| 4,728,265 A | 3/1988 | Cannon | |
| 5,542,826 A | 8/1996 | Warner | |
| 5,683,233 A * | 11/1997 | Moubayed ............. | F04B 43/12 |
| | | | 417/474 |
| 5,791,881 A * | 8/1998 | Moubayed ............ | F04B 43/082 |
| | | | 417/474 |
| 8,118,778 B2 | 2/2012 | Haylor et al. | |
| 2004/0193453 A1 * | 9/2004 | Butterfield ............ | G16H 40/60 |
| | | | 977/932 |
| 2009/0221964 A1 | 9/2009 | Rotem et al. | |

FOREIGN PATENT DOCUMENTS

| | | | | | |
|---|---|---|---|---|---|
| CN | 109125087 A | 1/2019 | | | |
| EP | 0239255 A1 * | 9/1987 | ............. | A61M 1/10 |
| KR | 20180002447 A | 1/2018 | | | |
| KR | 101 835 029 B1 | 3/2018 | | | |

* cited by examiner

SILENT PUMPING MECHANISM FOR INFUSION PUMP

CROSS-REFERENCE TO RELATED APPLICATIONS

This application is the national stage filing under 35 U.S.C. § 371 of International Application No. PCT/US2020/29359 filed Apr. 22, 2020, which claims priority to U.S. Provisional Application No. 62/837,529, filed on Apr. 23, 2019, the content of which are herein incorporated by reference in their entirety.

TECHNICAL FIELD

The current subject matter described herein relates generally to a pumping mechanism for an infusion pump and more particularly to a pumping mechanism for a peristaltic infusion pump.

BACKGROUND

Peristaltic infusion pumps are used for the administration of fluids to a patient and generally operate by providing a motion against a wall of a flexible tube containing fluid to be pumped to the patient. A controlled peristaltic action against the flexible tube allows for a controlled flow rate of the fluid. In certain types of peristaltic infusion pumps, the controlled peristaltic action is provided by a pumping mechanism that includes a number of pumping fingers that move in a coordinated and/or synchronized fashion with respect to one another to pump the fluid.

SUMMARY

Aspects of the current subject matter relate to a pumping mechanism for a peristaltic infusion pump, where the pumping mechanism includes one or more pumping fingers that move in a coordinated and synchronized fashion with respect to one another to provide a controlled peristaltic action against a flexible tube for delivery of a fluid to a patient.

According to aspects of the current subject matter, a pumping mechanism may include a cam including a central axis; a chassis including a recess within which the cam fits in a lengthwise extension along the central axis, where the recess includes a sidewall that defines an interior of the recess; and a plurality of fingers coupled to the cam and configured to move in a direction transverse to the central axis, where each of the plurality of fingers includes a body and a protrusion including a distal end and a proximal end, where the protrusion extends from the distal end outward from a side region of the body in a direction transverse to the direction of movement of the plurality of fingers such that the proximal end is in surface contact with the sidewall of the recess.

In an inter-related aspect, a peristaltic infusion pump may include a tubing receiver configured to receive tubing for infusing a fluid; and a pumping mechanism arranged to mechanically couple with the tubing and configured to act on at least a portion of the tubing to cause fluid flow through the tubing. The pumping mechanism may include a cam including a central axis; a chassis including a recess within which the cam fits in a lengthwise extension along the central axis, where the recess includes a sidewall that defines an interior of the recess; and a plurality of fingers coupled to the cam and configured to move in a direction transverse to the central axis, where each of the plurality of fingers includes a body and a protrusion including a distal end and a proximal end, where the protrusion extends from the distal end outward from a side region of the body in a direction transverse to the direction of movement of the plurality of fingers such that the proximal end is in surface contact with the sidewall of the recess.

In some variations, one or more of the features disclosed herein including the following features can optionally be included in any feasible combination. The distal end of the protrusion may be fitted within a cavity formed in the side region of the body. The pumping mechanism may further include a spring fitted within the cavity, where the distal end of the protrusion contacts the spring. The distal end of the protrusion may be removably fitted within the cavity. The proximal end of the protrusion may have a rounded edge. At least one of the plurality of fingers may include two protrusions, the two protrusions extending from opposing sides of the body of the at least one finger. The two protrusions may be off-axis with respect to one another. The distal end of the protrusion may be retractably connected to the side region of the body. The plurality of fingers may include four fingers positioned in a linear arrangement along the central axis of the cam. The four fingers may each include two protrusions, the two protrusions extending from opposing sides of the body of a corresponding finger of the four fingers.

The details of one or more variations of the subject matter described herein are set forth in the accompanying drawings and the description below. Other features and advantages of the subject matter described herein will be apparent from the description and drawings, and from the claims. The claims that follow this disclosure are intended to define the scope of the protected subject matter.

DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Aspects of the current subject matter relate to a pumping mechanism for a peristaltic infusion pump, where the pumping mechanism includes one or more pumping fingers that move in a coordinated and synchronized motion with respect to one another to provide a controlled peristaltic action against a flexible tube for delivery of a fluid to a patient. The pumping mechanism consistent with implementations of the current subject matter reduces or eliminates noise when in motion compared to traditional pumping mechanisms, by addressing vibrations of the pumping fingers that occur when in motion.

Before providing additional details regarding aspects of the pumping mechanism, the following provides a description of some examples of a patient care system and infusion pumps in which the pumping mechanism disclosed herein may be utilized. The following descriptions are meant to be exemplary, and aspects related to the pumping mechanism consistent with the current subject matter are not limited to the examples described herein.

Figure 1:
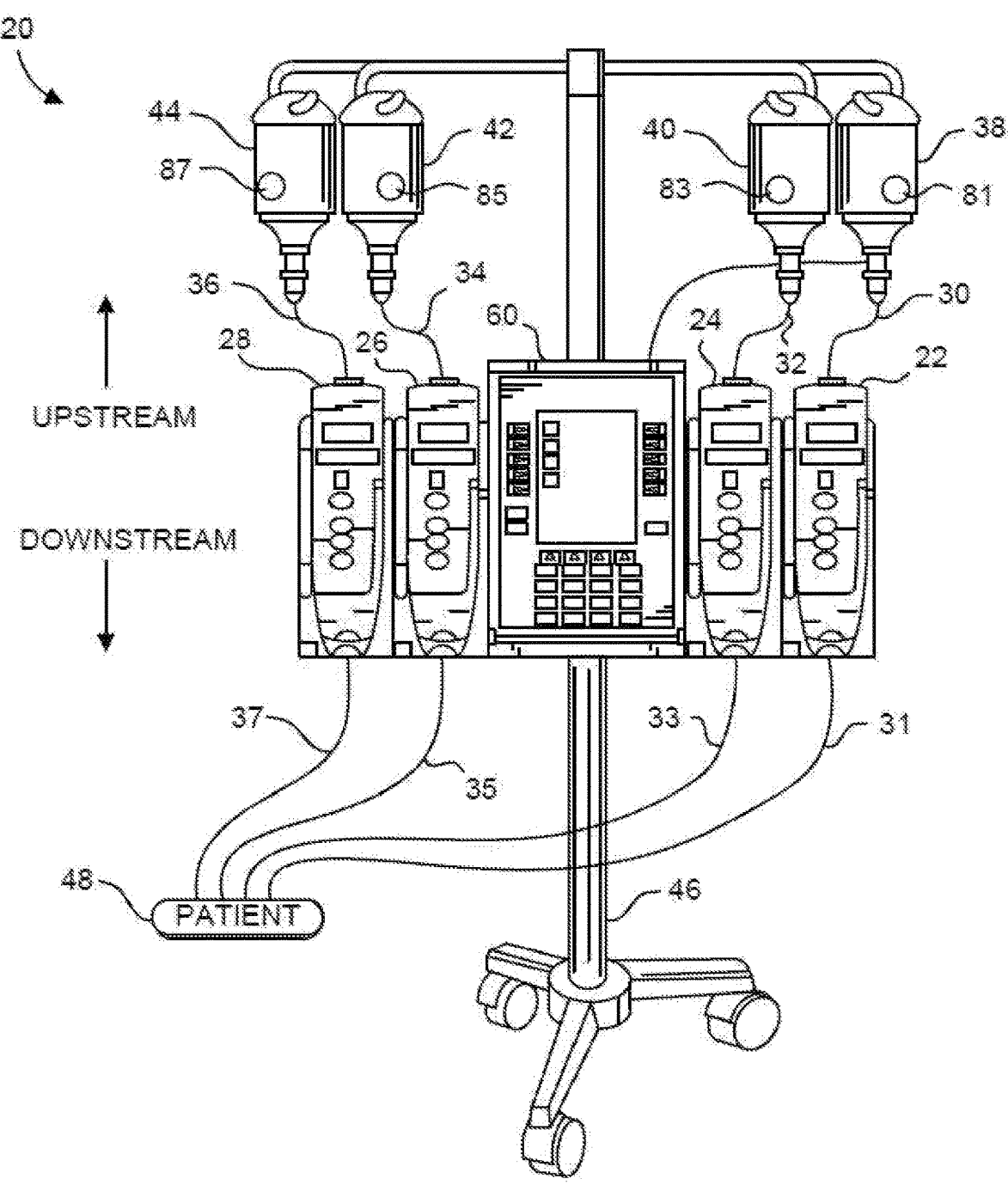
FIG. 1 is a front view of a patient care system having four fluid infusion pumps, each of which is connected to a respective fluid supply for pumping contents of the fluid supply to a patient, in which aspects of the current subject matter may be employed.

Referring now in more detail to the drawings in which like reference numerals refer to like or corresponding elements among the several views, there is shown in FIG. 1 a patient care system 20 having four infusion pumps 22, 24, 26, and 28 each of which is fluidly connected with an upstream fluid line 30, 32, 34, and 36, respectively. Each of the four infusion pumps 22, 24, 26, and 28 is also fluidly connected with a downstream fluid line 31, 33, 35, and 37, respectively. The fluid lines can be any type of fluid conduit, such as tubing, through which fluid can flow.

Fluid supplies 38, 40, 42, and 44, which may take various forms but in this case are shown as bottles, are inverted and suspended above the pumps. Fluid supplies may also take the form of bags or other types of containers. Both the patient care system 20 and the fluid supplies 38, 40, 42, and 44 are mounted to a roller stand or IV pole 46.

A separate infusion pump 22, 24, 26, and 28 is used to infuse each of the fluids of the fluid supplies into the patient. The infusion pumps are flow control devices that will act on the respective fluid line to move the fluid from the fluid supply through the fluid line to the patient 48. Because individual pumps are used, each can be individually set to the pumping or operating parameters required for infusing the particular medical fluid from the respective fluid supply into the patient at the particular rate prescribed for that fluid by the physician. Such medical fluids may comprise drugs or nutrients or other fluids.

Typically, medical fluid administration sets have more parts than are shown in FIG. 1. Many have check valves, drip chambers, valved ports, connectors, and other devices well known to those skilled in the art. These other devices have not been included in the drawings so as to preserve clarity of illustration. In addition, it should be noted that the drawing of FIG. 1 is not to scale and that distances have been compressed for the purpose of clarity. In an actual setting, the distance between the bottles 38, 40, 42, and 44 and the infusion pump modules 22, 24, 26, and 28 could be much greater.

Figure 2:
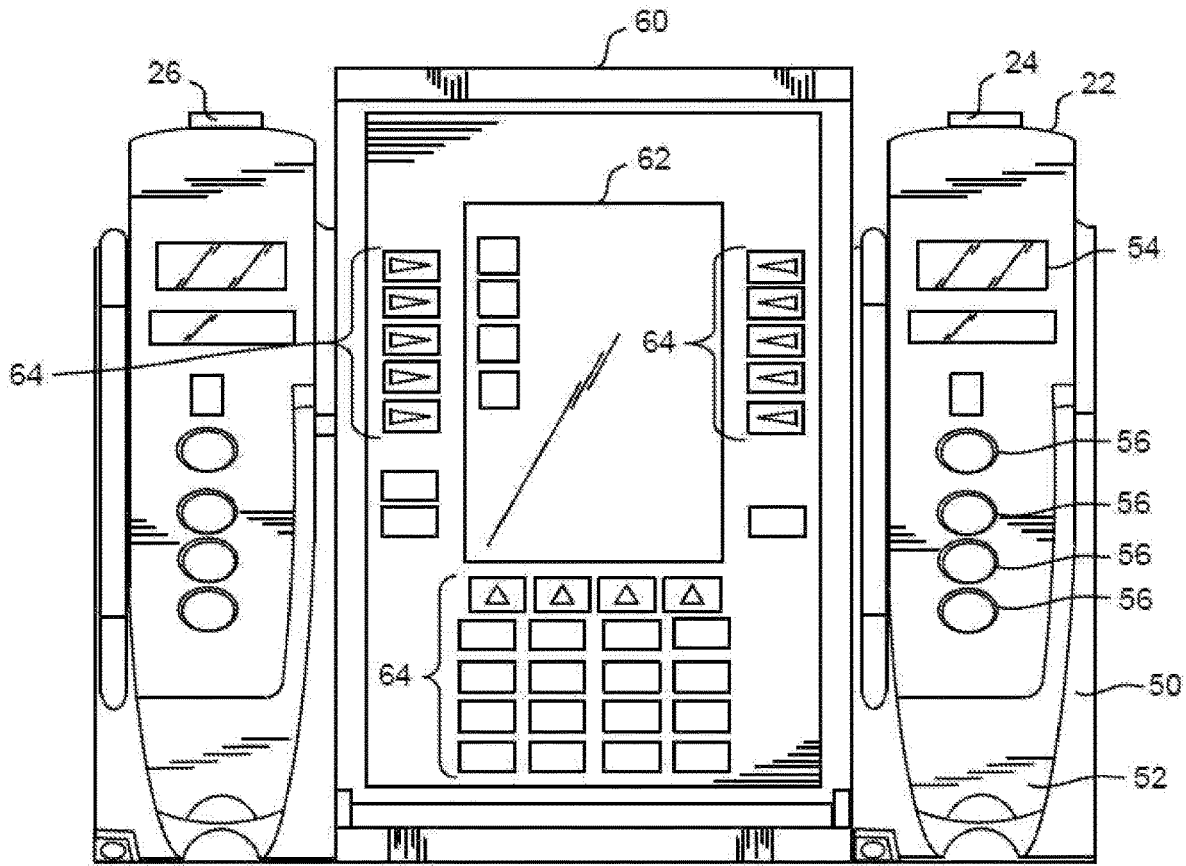
FIG. 2 is an enlarged view of a portion of the patient care system of FIG. 1 showing two of the fluid infusion pumps mounted at either side of a programming module, and the displays and control keys of each, with the programming module being capable of programming both infusion pumps.

Referring now to FIG. 2, an enlarged view of the front of the infusion pump 24 is shown. The pump includes a front door 50 and a handle 52 that operates to lock the door in a closed position for operation and to unlock and open the door for access to the internal pumping and sensing mechanisms and to load administration sets for the pump. When the door is open, the tube can be connected with the pump, as described with reference to FIG. 3. When the door is closed, the tube is brought into operating engagement with the pumping mechanism, the upstream and downstream pressure sensors, and the other equipment of the pump. A display 54, such as an LED display, is located in plain view on the door in this embodiment and may be used to visually communicate various information relevant to the pump, such as alert indications (e.g., alarm messages). Control keys 56 exist for programming and controlling operations of the infusion pump as desired. The infusion pump 24 also includes audio alarm equipment in the form of a speaker (not shown).

In the implementation shown, a programming module 60 is attached to the left side of the infusion pump 24. Other devices or modules, including another infusion pump, may be attached to the right side of the infusion pump 24, as shown in FIG. 1. In such a system, each attached pump represents a pump channel of the overall patient care system 20. The programming module may be used to provide an interface between the infusion pump 24 and external devices as well as to provide most of the operator interface for the infusion pump 24.

The programming module 60 includes a display 62 for visually communicating various information, such as the operating parameters of the pump 24 and alert indications and alarm messages. The programming module 60 may also include a speaker to provide audible alarms. The programming module or any other module also has various input devices in this embodiment, including control keys 64 and a bar code or other scanner or reader for scanning information from an electronic data tag relating to the infusion, the patient, the care giver, or other. The programming module also has a communications system (not shown) with which it may communicate with external equipment such as a medical facility server or other computer and with a portable processor, such as a handheld portable digital assistant ("PDA"), or a laptop-type of computer, or other information device that a care giver may have to transfer information as well as to download drug libraries to a programming module or pump.

The communications system may take the form of a radio frequency ("RF") (radio frequency) system, an optical system such as infrared, a Bluetooth system, or other wired or wireless system. The bar code scanner and communications system may alternatively be included integrally with the infusion pump 24, such as in cases where a programming module is not used, or in addition to one with the programming module. Further, information input devices need not be hard-wired to medical instruments, information may be transferred through a wireless connection as well.

FIG. 2 includes a second pump module 26 connected to the programming module 60. As shown in FIG. 1, more pump modules may be connected. Additionally, other types of modules may be connected to the pump modules or to the programming module.

Figure 3:
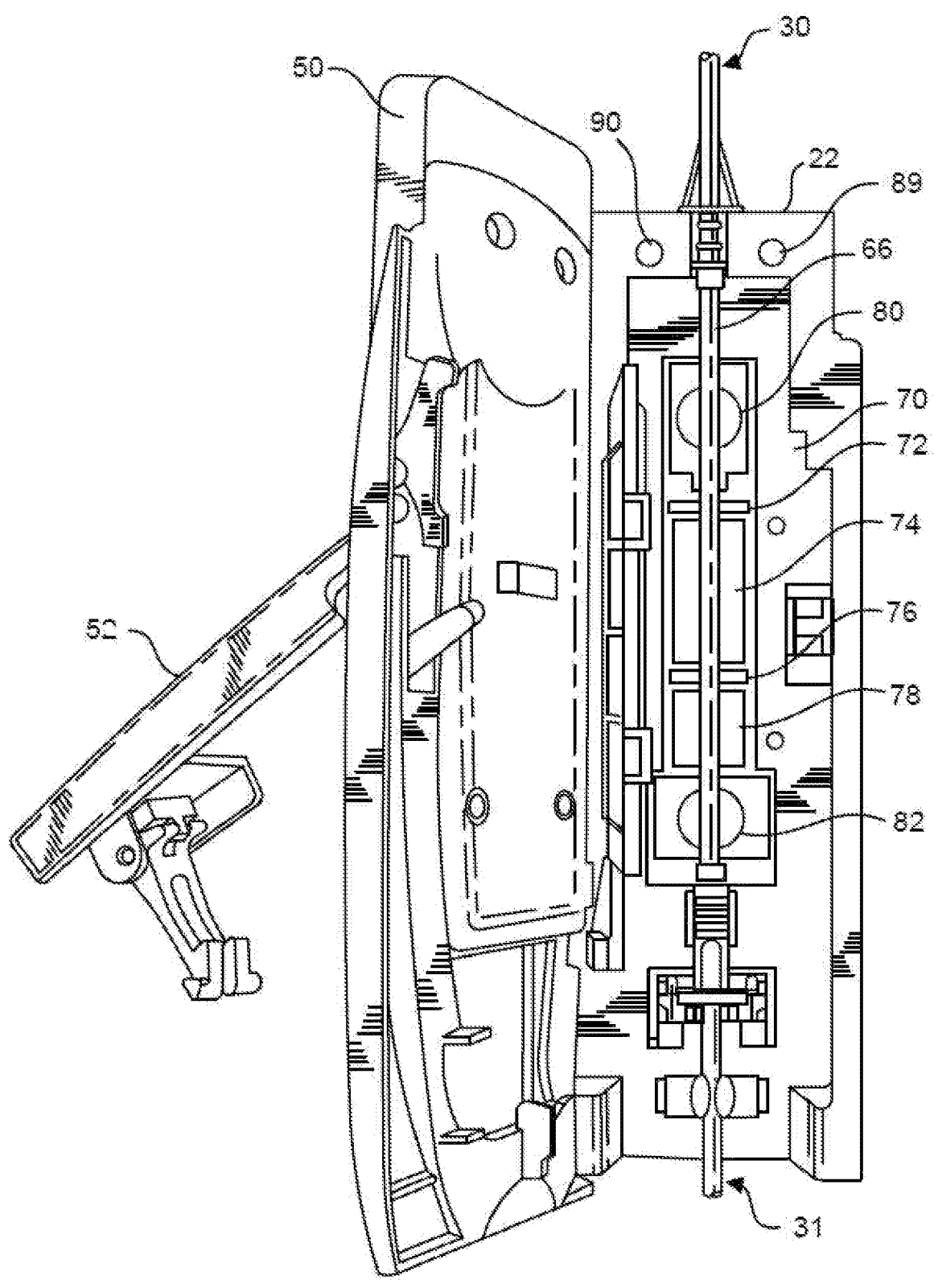
FIG. 3 is a perspective view of one of the fluid infusion pumps of FIG. 1 and FIG. 2 with its front door in an open position.

Turning now to FIG. 3, an infusion pump 22 is shown in perspective view with the front door 50 open, showing the upstream fluid line 30 and downstream fluid line 31 in operative engagement with the pump 22. The infusion pump 22 directly acts on a tube 66 (also referred to as a pump segment) that connects the upstream fluid line 30 to the downstream fluid line 31 to form a continuous fluid conduit, extending from the respective fluid supply 38 (FIG. 1) to the patient 48, through which fluid is acted upon by the pump to move fluid downstream to the patient. Specifically, a pumping mechanism 70 acts as the flow control device of the pump to move fluid though the conduit. The upstream and downstream fluid lines and/or tube 66 may be coupled to a pump cassette or cartridge that is configured to be coupled to the pump 2, such as the type described in co-pending U.S. patent application Ser. No. 13/827,775, which is incorporated by reference herein.

The pumping mechanism may be, for example, a multiple finger peristaltic pumping mechanism. For example, the pumping mechanism may be of the "four finger" type and includes an upstream occluding finger (first finger) 72, a primary pumping finger (second finger) 74, a downstream occluding finger (third finger) 76, and a secondary pumping finger (fourth finger) 78. The four finger pumping mechanism and mechanisms used in other linear peristaltic pumps operate by sequentially pressing on a segment of the fluid conduit by means of a cam and the fingers 72, 74, 76, 78. Pressure is applied in sequential locations of the conduit, beginning at the upstream end of the pumping mechanism and working toward the downstream end. At least one finger is always pressing hard enough to occlude the conduit. As a practical matter, one finger does not retract from occluding the tubing until the next one in sequence has already occluded the tubing; thus at no time is there a direct fluid path from the fluid supply to the patient. The operation of peristaltic pumps including four finger pumps is well known to those skilled in the art.

FIG. 3 further shows a downstream pressure sensor 82 included in the pump 22 at a downstream location with respect to the pumping mechanism. The downstream pressure sensor 82 is mounted to the flow control device (the pumping mechanism 70) and is located adjacent and downstream in relation to the flow control device. The downstream pressure sensor is located downstream from the flow control device, that is, at a location between the patient 48 (FIG. 1) and the flow control device, so that the connection of the correct fluid supply with the correct pump may be verified before any fluid is pumped to the patient.

With reference still to FIG. 3, an upstream pressure sensor 80 may also be included in the pump 22. The upstream pressure sensor is assigned to the flow control device or pumping mechanism 70 and, in this embodiment, is further provided as an integral part of the pump 22. It is mounted to the pumping mechanism 70 and is located adjacent and upstream in relation to the flow control device. The upstream pressure sensor is located upstream from the flow control device, that is, at a location between the fluid supply 38 (FIG. 1) and the flow control device, so that the connection of the correct fluid supply with the correct pump may be verified before any fluid is pumped to the patient.

Figure 4:
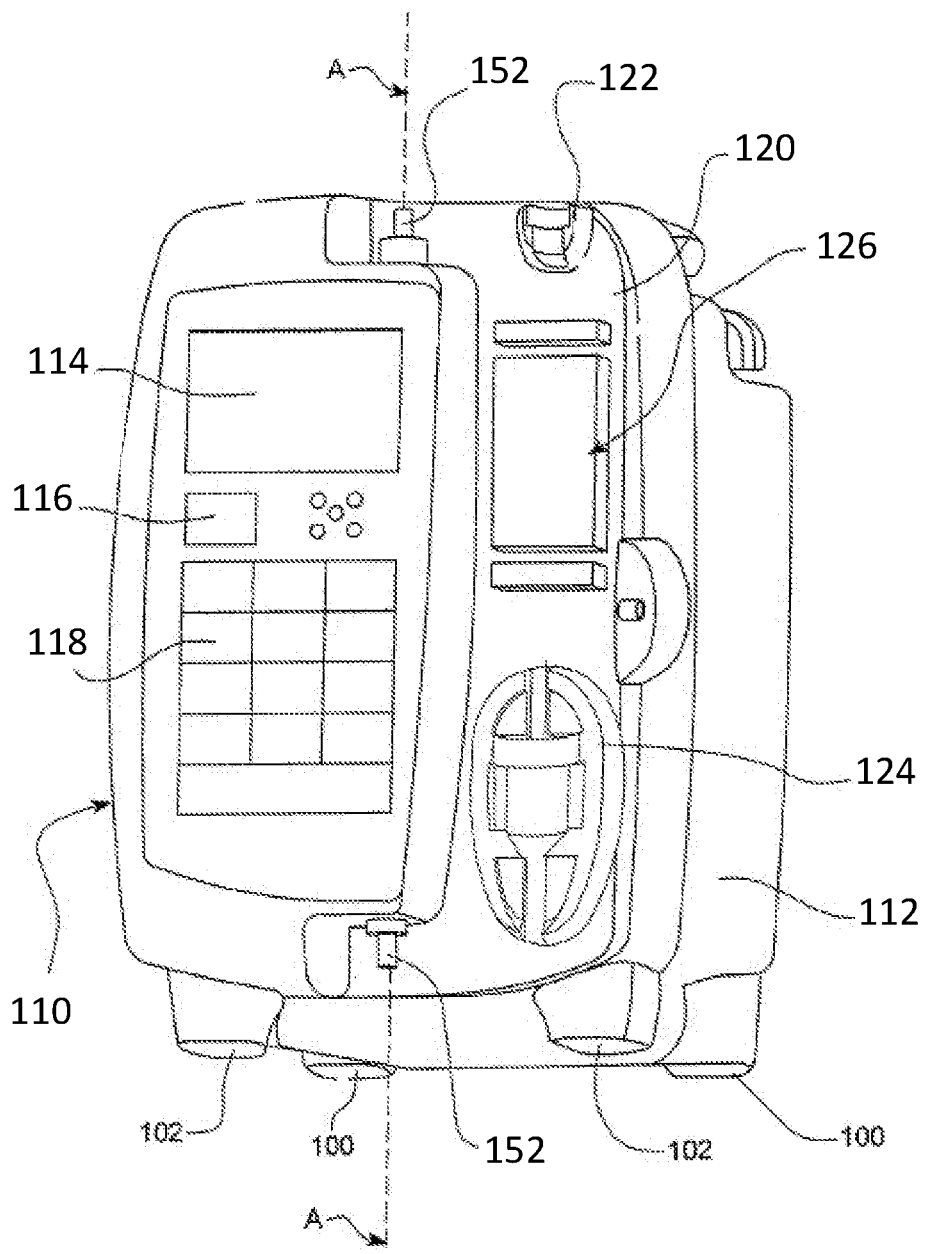
FIG. 4 is a perspective view of an alternative infusion pump unit, with a removable door removed, in which aspects of the current subject matter may be employed.
Figure 5:
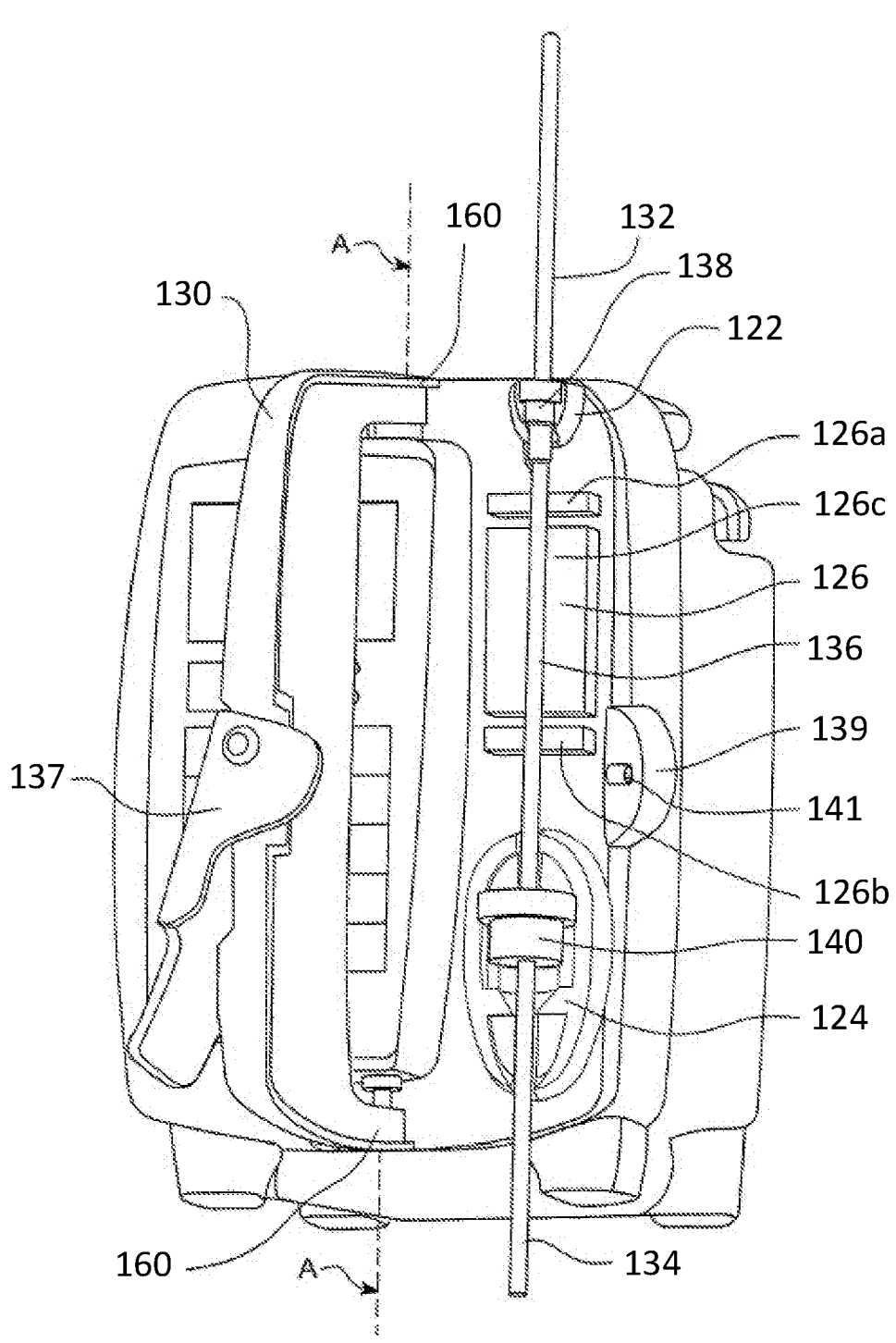
FIG. 5 is a perspective view of the infusion pump unit of FIG. 4, with the removable door in place and in an open position.

Now with reference to FIG. 4 and FIG. 5, an alternative infusion pump unit in which aspects of the current subject matter may be employed is described. FIG. 4 is a perspective view of an infusion pump unit with a removable door removed, and FIG. 5 is a perspective view of the infusion pump unit of FIG. 4, with the removable door in place and in an open position.

With reference to FIG. 4 and FIG. 5, an infusion system for parenteral infusion of a medical fluid to a patient includes a pump unit 110, a major part of which includes a housing 112 which accommodates, in manner known per se, a cam mechanism controlling a plurality of fingers of a peristaltic pumping mechanism, an electric motor and associated gearing, driving said cam mechanism, and further accommodates electronic control and processing circuitry for controlling such motor and processing signals from pressure sensors etc. provided on the unit. The pump unit, as shown, may also include an electronically operated display 114, an alarm light 116, an input keyboard 118 or other manually operated controls, all in manner known per se.

As shown in FIG. 4 and FIG. 5, on the front of the housing there is provided a face or deck 120 on which is exposed an upper mounting or bracket 122 for a complementary fitting 138 forming part of an infusion line; a lower mounting or bracket 124 for a complementary fitting 140 forming part of such infusion line and a peristaltic assembly 126 which is, effectively, the operative end of the peristaltic pumping mechanism and may, in principle, be the free ends of respective fingers moveable, by the cam mechanism referred to, inwards and outwards from the face or deck 120. In order to make it easier to maintain sterile conditions, these fingers may be covered by a thin flexible membrane, (not shown), sealed at its edges with respect to the deck 120. As shown in FIG. 5, a door 130 is normally fitted to the housing 112 and can be swung between an open position and a closed position, about a pivotal axis A. A medical fluid infusion line, for use with the pump unit, includes upper and lower sections 132 and 134 respectively of transparent plastics tubing, an intermediate section 136 of resiliently compressible tubing, for example of silicone rubber, and upper and lower fittings 138 and 140 via which the tubing section 136 is connected respectively with the upper line 132 and with the lower line 134. In use, the upper line 132 extends upwardly to a source of the medical fluid to be administered whilst the lower line 134 extends from the infusion pump to an infusion needle or the like inserted into the patient. In use, the infusion line is extended across the face or deck 120 of the pump unit so that the fittings 130 and 140 are received in the brackets 122 and 124 respectively and so that the tubing section 136 extends over the peristaltic assembly 126 as illustrated in FIG. 5. The infusion line is fitted in place in this fashion whilst the door 130 is in the open position shown in FIG. 5. After the infusion line has been so fitted, the door 130 is moved to the closed position and is secured by a catch 137 which includes a lever mounted on the outer edge of the door 130 (i.e., the edge which lies at the side of the pump unit when the door is in its closed position). The catch 137 is configured to engage a boss 141 projecting laterally from the pump housing into recess 139.

In operation of the pump, in known manner, the fingers of the peristaltic assembly 126 periodically press the flexible resilient tubing against a counter surface or anvil to propel fluid within the infusion line along the latter. In the pump shown, the peristaltic assembly includes an upper finger 126a and a lower finger 126b which are of a relatively limited extent in the longitudinal direction of the infusion line, and an intermediate finger or pad 126c, between the upper and lower fingers and which finger 126c is extended or elongated in the longitudinal direction of the infusion line. In operation, assuming the fluid is to be propelled downwards, as viewed in FIG. 4 and FIG. 5, along the infusion line, the peristaltic assembly performs a repeating cycle in which, with the intermediate pad 126c spaced from the counter surface, the upper finger presses the flexible tube against the counter surface or anvil to close the tube at the location of the upper finger 126a, the lower finger is then withdrawn from the counter surface to open the tube at the location of the lower finger 126*b*, then the intermediate pad or finger 126*c* is moved towards the counter surface to drive the fluid in the tube adjacent the intermediate pad 126*c* downward along the tube, then the tube is pinched closed again between the lower finger 126*b* and the counter surface, then the upper finger 126*a* is withdrawn from the counter surface and the intermediate finger 126*c* withdrawn from the counter surface to draw fresh fluid into the part of the tube adjacent the intermediate finger 126*c*. Also shown in FIG. 4 and FIG. 5 are feet 100, 102, for example of elastomeric material, for use when the unit is to be supported on a flat surface rather than, for example, clamped to a rail; hinge pins 152; and lever 160.

The following description with reference to FIG. 6-FIG. 8B refers to aspects of the pumping mechanism 70 and the four fingers 72, 74, 76, 78 as shown and described with reference to FIG. 1-FIG. 3. However, aspects of the pumping mechanism consistent with the current subject matter are not limited to the patient care system and fluid infusion pumps of FIG. 1-FIG. 3. Rather, aspects of the current subject matter may be applied to various other care systems, infusion pumps, and other pumps that employ a peristaltic pumping mechanism. Moreover, aspects of the current subject matter are not limited to peristaltic pumping mechanisms with four fingers. Rather, aspects of the current subject matter may be applied to a pumping mechanism with a single finger or multiple fingers. For example, aspects of the current subject matter may be employed in the infusion pump described with reference to FIG. 4 and FIG. 5.

Figure 6:
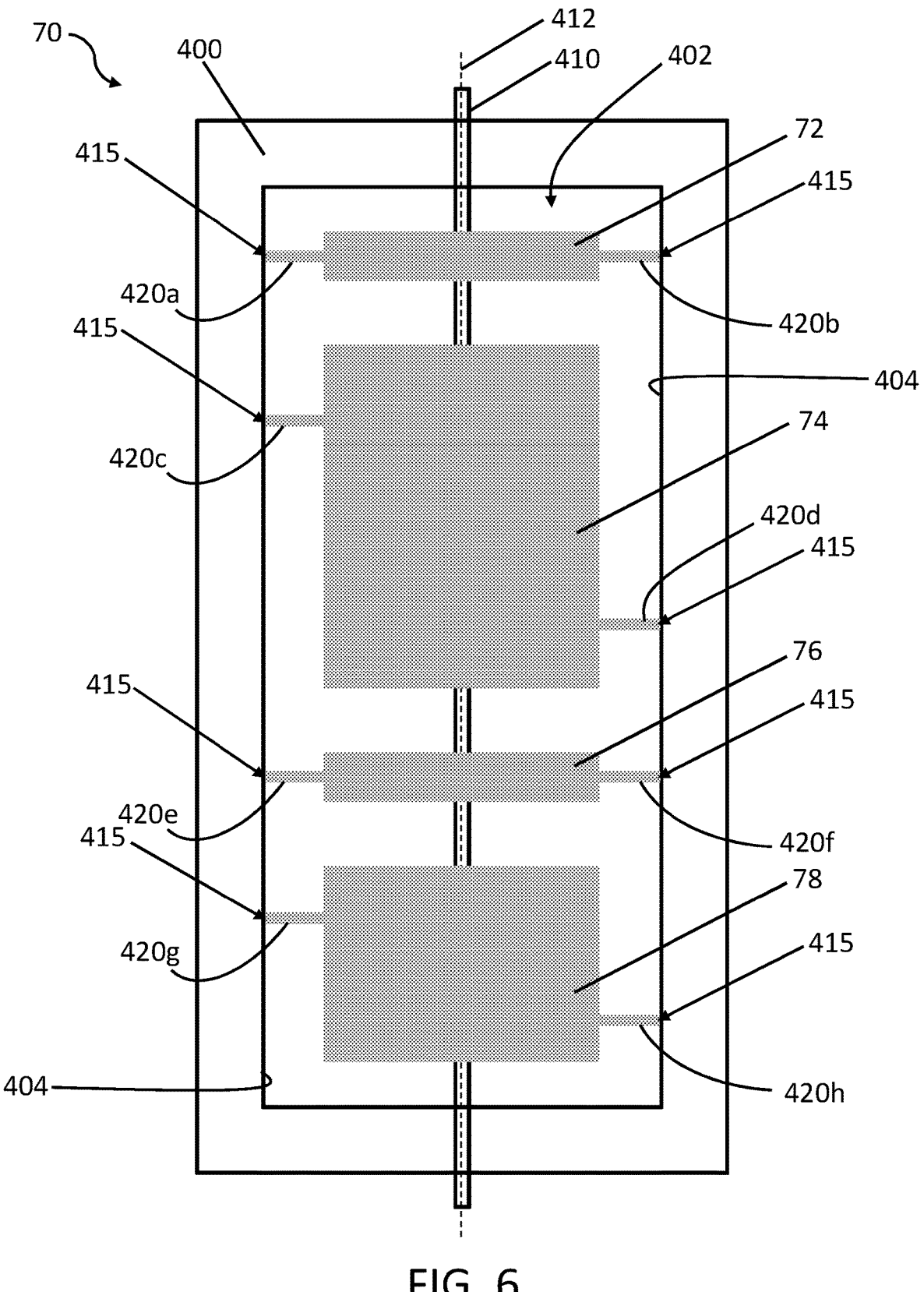
FIG. 6 is an example representation of a top view of a pumping mechanism consistent with implementations of the current subject matter.
Figure 7A:
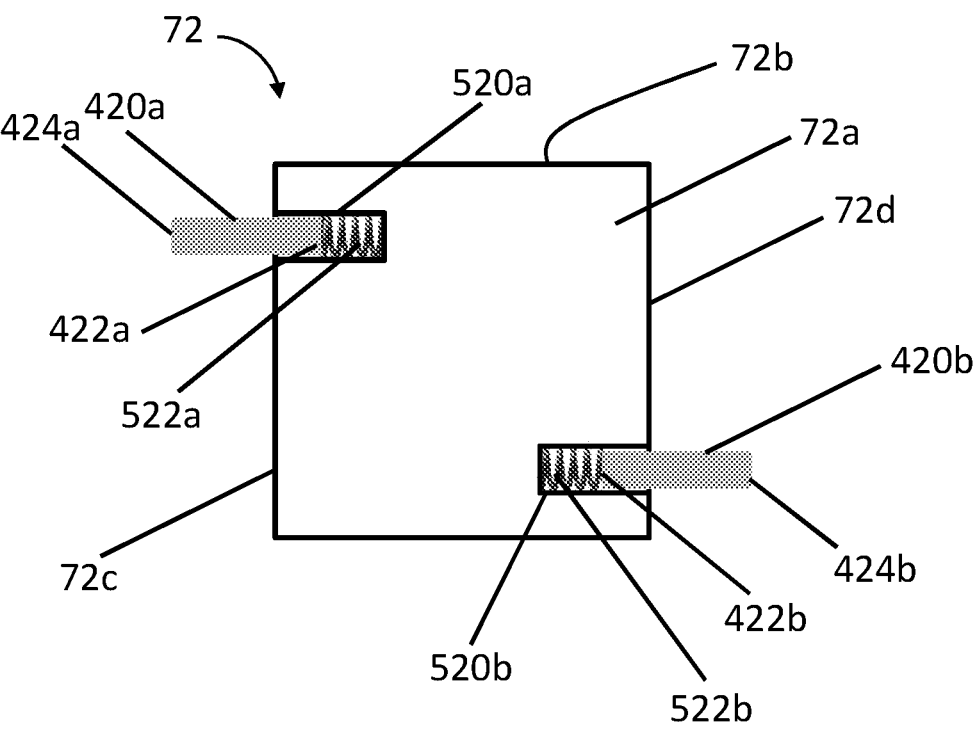
FIG. 7A-FIG. 7D are example representations of cross-sectional front views of fingers of a pumping mechanism consistent with implementations of the current subject matter.
Figure 7B:
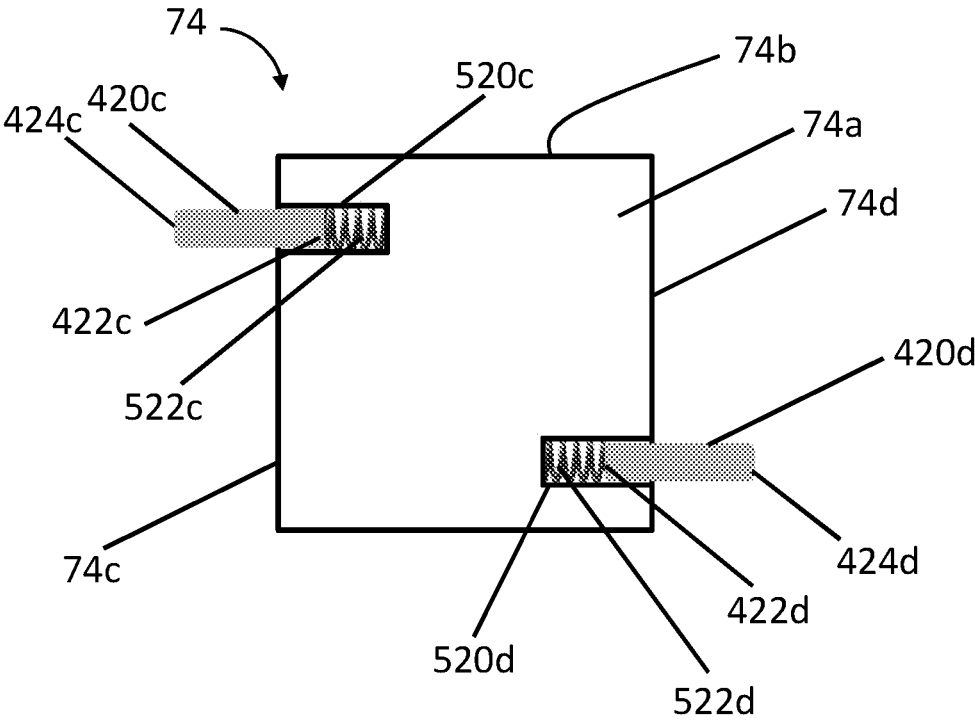
Figure 7C:
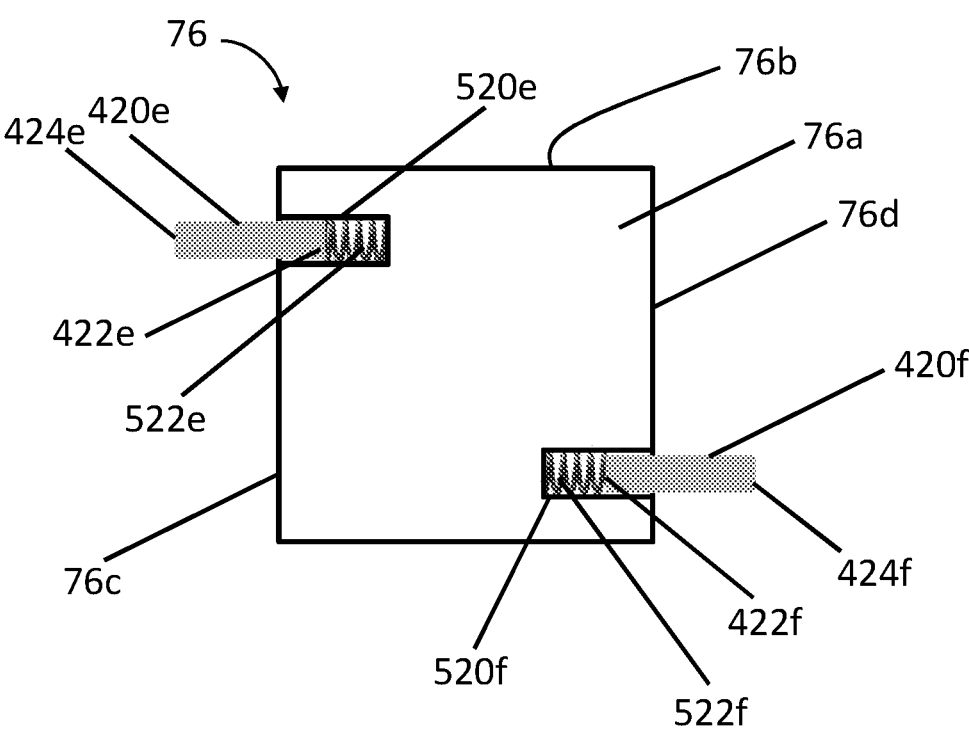
Figure 7D:
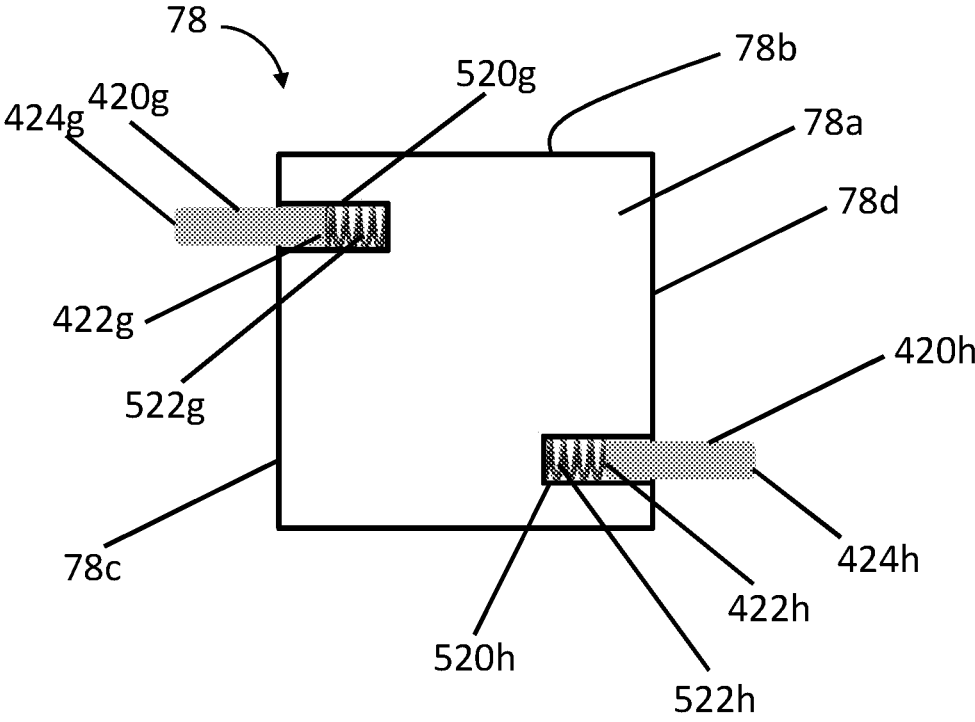

Now with reference to FIG. 6, details of the pumping mechanism 70 and the four fingers 72, 74, 76, 78 consistent with implementations of the current subject matter are provided. In particular, FIG. 6 provides a top view of the pumping mechanism 70. A chassis 400 is provided and includes a recess 402 with sidewalls 404 that define an interior region of the recess 402. A cam 410 having a central axis 412 fits at least partially within the recess 402 of the chassis 400. In particular, the cam 410 extends in a lengthwise direction along the central axis 412 within the recess 402. The fingers 72, 74, 76, 78 are each mechanically coupled to the cam 410 and are configured to move in a direction transverse to the central axis 412. In particular, the fingers 72, 74, 76, 78 are configured to move outward and inward (i.e., up and down) with respect to an opening of the recess 402. The fingers 72, 74, 76, 78 may be of varying sizes and shapes. The sizes and shapes of the fingers 72, 74, 76, 78 are such that the fingers 72, 74, 76, 78 are able to provide the appropriate peristaltic action against the tube 66 for delivery of a fluid to the patient 48. Additional features of the cam 410 and the coupling of the fingers 72, 74, 76, 78 to the cam 410, including the operation and movements of the cam 410 and the fingers 72, 74, 76, 78, as they pertain to peristaltic pumps are well known to those of ordinary skill in the art.

The recess 402 of the chassis 400 may be shaped such that the cam 410 and the fingers 72, 74, 76, 78 coupled thereto are able to be placed or fitted within the recess 402. Moreover, the recess 402 is shaped and sized to allow for the proper movement of the cam 410 and the fingers 72, 74, 76, 78 to provide the peristaltic action of the pumping mechanism 70. The recess 402 may have a non-uniform cross-section with portions of the recess 402 wider and/or deeper at some points than at other points such that the cam 410 and each of the fingers 72, 74, 76, 78 fit and move within the recess 402. In some instances, the recess 402 may be shaped and sized such that an arrangement of the cam 410 and the fingers 72, 74, 76, 78 is aligned or at least partially aligned with edges of the sidewalls 404 of the recess 402. In such an implementation, a gap or a space may exist between edges of the fingers 72, 74, 76, 78 and the sidewalls 404. In other instances, the recess 402 may have a uniform cross-section, for example a rectangular cross-section. In this implementation, a gap is also present between the edges of the fingers 72, 74, 76, 78 and the sidewalls 404.

Implementations of the current subject matter provide for at least a portion of the fingers 72, 74, 76, 78 to have a point of contact 415 with a surface of the sidewalls 404 of the recess 402. Consistent with implementations of the current subject matter, the points of contact 415 are flexible, for example retractable, points. The points of contact 415 provide a steadying and/or stabilizing force to the fingers 72, 74, 76, 78 such that as the fingers 72, 74, 76, 78 move up and down within the recess 402, the points of contact 415 reduce or eliminate vibration of the fingers 72, 74, 76, 78. For example, the pumping movement of the fingers 72, 74, 76, 78 may result in vibration thereof. The vibration may cause side regions or edges of the fingers 72, 74, 76, 78 to come into contact with the sidewalls 404 in the gap or space there between, which may result in an unwanted and/or undesirable noise, for example, the fingers 72, 74, 76, 78 tapping or bumping against or otherwise engaging the sidewalls 404 in a repeated motion. Consistent with implementations of the current subject matter, the points of contact 415 eliminate or greatly reduce the vibrations of the fingers 72, 74, 76, 78 against the sidewalls 404 by stabilizing the fingers 72, 74, 76, 78 with respect to the sidewalls 404. Moreover, the points of contact 415 do not hinder or impede movement of the fingers 72, 74, 76, 78. Instead, as the points of contact 415 move with the fingers 72, 74, 76, 78, the points of contact 415 remain in contact with the sidewalls 404 as a stabilizing force as the fingers 72, 74, 76, 78 move up and down within the recess 402.

As shown in FIG. 6, the points of contact 415 are provided by protrusions 420 that extend outward from a side region of the fingers 72, 74, 76, 78 such that proximal ends of the protrusions 420 are in surface contact with the sidewalls 404. Distal end of the protrusions are in contact with side regions of the fingers 72, 74, 76, 78.

FIG. 7A, FIG. 7B, FIG. 7C, and FIG. 7D are example representations of cross-sectional front views of the fingers 72, 74, 76, 78, respectively, consistent with implementations of the current subject matter. The example representations do not include any coupling components that may be part of the fingers 72, 74, 76, 78 for coupling to the cam 410, as such components are well known to those of ordinary skill in the art and are not necessary for the description of the current subject matter. The fingers 72, 74, 76, 78 may be of other shapes and sizes than those shown and described herein. For example, the fingers 72, 74, 76, 78 are depicted herein as having primarily rectangular surface areas for ease in describing implementations of the current subject matter as it relates to the pumping mechanism 70. However, the fingers 72, 74, 76, 78 may take the form of other shapes and may have varying profiles or cross-sections without departing from the scope of the current subject matter. Additionally, while the fingers 72, 74, 76, 78 are depicted as being substantially solid throughout, the fingers 72, 74, 76, 78 consistent with implementations of the current subject matter are not so limited.

Each of the fingers 72, 74, 76, 78 has a body 72*a*, 74*a*, 76*a*, 78*a* with an upper region 72*b*, 74*b*, 76*b*, 78*b*, respectively. The upper regions 72*b*, 74*b*, 76*b*, 78*b* are the portions of the fingers 72, 74, 76, 78 shown in FIG. 3 and FIG. 4 (i.e., the upward exposed tops of the fingers). Each body 72*a*, 74*a*, 76*a*, 78*a* has side regions 72*c*,*d*, 74*c*,*d*, 76*c*,*d*, 78*c*,*d*, respectively. The protrusions 420 extend from the side regions 72*c*,*d*, 74*c*,*d*, 76*c*,*d*, 78*c*,*d*. Shown are protrusions 420*a*, 420*b*, 420*c*, 420*d*, 420*e*, 420*f*, 420*g*, 420*h* (i.e., two protrusions 420 per each finger 72, 74, 76, 78). However, the pumping mechanism 70 is not limited to this configuration and more or fewer protrusions 420 may be part of the pumping mechanism 70 consistent with implementations of the current subject matter. For example, each finger 72, 74, 76, 78 is not required to have two protrusions 420. In some instances, one or more fingers 72, 74, 76, 78 may have one protrusion 420. In some instances, one or more fingers 72, 74, 76, 78 may have more than two protrusions 420.

Each protrusion 420 has a distal end 422 and a proximal end 424. Shown in the representations of FIG. 7A-FIG. 7D are the distal ends 422*a*, 422*b*, 422*c*, 422*d*, 422*e*, 422*f*, 422*g*, 422*h;* and the proximal ends 424*a*, 424*b*, 424*c*, 424*d*, 424*e*, 424*f*, 424*g*, 424*h*. The protrusions 420 attach to the respective fingers 72, 74, 76, 78 by way of, for example, a cavity 520 formed in the side regions 72*c*,*d*, 74*c*,*d*, 76*c*,*d*, 78*c*,*d*. Shown are cavities 520*a*, 520*b*, 520*c*, 520*d*, 520*e*, 520*f*, 520*g*, 520*h* that correspond to the protrusions 420*a*, 420*b*, 420*c*, 420*d*, 420*e*, 420*f*, 420*g*, 420*h*.

Consistent with implementations of the current subject matter and as shown in FIG. 7A-FIG. 7D, a spring 522 is fitted within each cavity 520. Shown are springs 522*a*, 522*b*, 522*c*, 522*d*, 522*e*, 522*f*, 522*g*, 522*h*. Each spring 522 occupies a volume of the cavity 520 such that the spring 522 is compressed within the cavity 520 upon insertion of the protrusion 420. Each cavity 520 is sized and shaped to allow for a corresponding protrusion 420 to fit and be held securely within the cavity 520 and to engage a corresponding spring 522. The size and shape of the cavity 520 and the size and shape of the protrusion 420 are such that the protrusion 420 removably fits within the cavity 520 and that movement of the protrusion 420 (i.e., lateral movement of the protrusion 420 out of the cavity 520) is not prevented by placement of the protrusion 420 within the cavity 520. That is, there is a small clearance of space between an outer circumference of the protrusion 420 and an inner circumference of the cavity 520. The spring 522 thus provides a flexible, retractable fit of the protrusion 420 within the cavity 520. The flexible, retractable fit of the protrusion 420 within the cavity 520 provides for the points of contact 415 between the protrusion 420 and the sidewalls 404 of the chassis 400, as shown in FIG. 6.

Each protrusion 420 and each cavity 520 may have a circular circumference, such that the protrusion is a type of round peg that fits within a circular opening. Other cross-sections, for example oval or square, may be utilized consistent with implementations of the current subject matter. The distal ends 422*a*, 422*b*, 422*c*, 422*d*, 422*e*, 422*f*, 422*g*, 422*h* may be flat or substantially flat, and the proximal ends 424*a*, 424*b*, 424*c*, 424*d*, 424*e*, 424*f*, 424*g*, 424*h* may be rounded or otherwise curved to provide a direct contact point with the sidewalls 404 of the chassis 400.

Figure 8A:
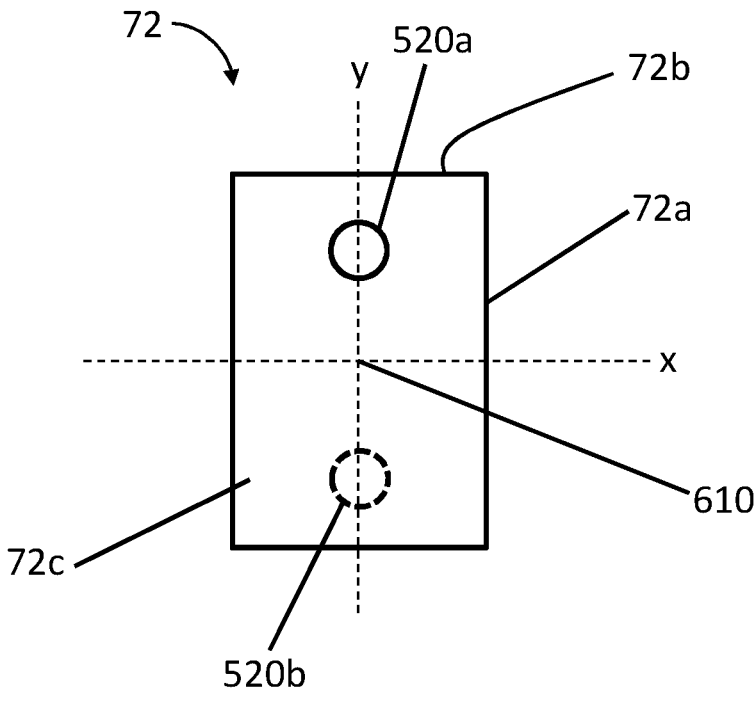
FIG. 8A-FIG. 8B are example representations of side views of fingers of a pumping mechanism consistent with implementations of the current subject matter.
Figure 8B:
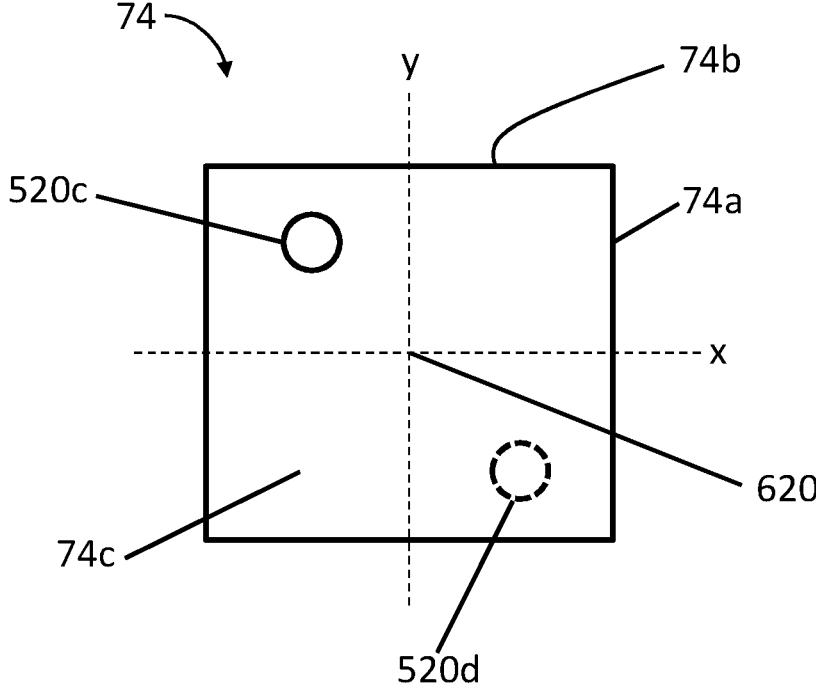

FIG. 8A-FIG. 8B are example representations of side views of the fingers 72 and 74 respectively of the pumping mechanism 70 consistent with implementations of the current subject matter. FIG. 8A illustrates the side region 72*c*, and FIG. 8B illustrates the side region 74*c*. Shown in FIG. 8A are the cavities 520*a* and 520*b*, with the cavity 520*b* in dashed lines to signify that the cavity 520*b* is on the opposing side, the side region 72*d*, of the finger 72. The cavities 520*a* and 520*b* are off-axis along the horizontal x-axis with respect to one another. For example, the cavities

520*a* and 520*b* may be positioned an equal distance along the vertical y-axis with respect to a middle point 610. This arrangement may provide for increased stability of the finger 72 with respect to the sidewalls 404 of the chassis 400 by, for example, providing opposing points of contact that are spaced apart. Additional positions and arrangements of the cavities 520*a* and 520*b* may be utilized such that the finger 72 is adequately stabilized with respect to the sidewalls 404.

Shown in FIG. 8B are the cavities 520*c* and 520*d*, with the cavity 520*d* in dashed lines to signify that the cavity 520*d* is on the opposing side, the side region 74*d*, of the finger 74. The cavities 520*c* and 520*d* are off-axis along the horizontal x-axis and the vertical y-axis with respect to one another. For example, the cavities 520*c* and 520*d* may be positioned an equal distance along the vertical y-axis and along the horizontal x-axis with respect to a middle point 620. This arrangement may provide for increased stability of the finger 74 with respect to the sidewalls 404 of the chassis 400 by, for example, providing opposing points of contact that are spaced apart. Additional positions and arrangements of the cavities 520*c* and 520*d* may be utilized such that the finger 74 is adequately stabilized with respect to the sidewalls 404.

Consistent with implementations of the current subject matter dimensions of the protrusions 420*a*, 420*b*, 420*c*, 420*d*, 420*e*, 420*f*, 420*g*, 420*h* may be within a range of various diameters or thicknesses and various lengths and may be dependent on the size of the body of the respective finger. For example, a particular protrusion 420 needs to be large enough (with respect to both thickness and length) to provide adequate stability and support for the respective finger, while also not being too large (i.e., the proximal end 424 having too large of a surface area) in which case the protrusion 420 may introduce an amount of friction between the finger and the sidewall 404 that impedes movement of the finger. In some implementations, the protrusions 420*a*, 420*b*, 420*c*, 420*d*, 420*e*, 420*f*, 420*g*, 420*h* may have a diameter or thickness that is between 10% and 25% of a length of the body of the finger on which the protrusion is mounted or affixed. In some implementations, the protrusions 420*a*, 420*b*, 420*c*, 420*d*, 420*e*, 420*f*, 420*g*, 420*h* may have a length that is at or below 50% of a width of the body of the finger.

As previously described, the cavities 520*a*, 520*b*, 520*c*, 520*d*, 520*e*, 520*f*, 520*g*, 520*h* may be required to have an inner circumference slightly larger than that of the outer circumference of the protrusions 420*a*, 420*b*, 420*c*, 420*d*, 420*e*, 420*f*, 420*g*, 420*h* to provide for the flexible, retractable fit of the protrusions 420*a*, 420*b*, 420*c*, 420*d*, 420*e*, 420*f*, 420*g*, 420*h* within the respective cavities 520*a*, 520*b*, 520*c*, 520*d*, 520*e*, 520*f*, 520*g*, 520*h*. In some implementations the difference between the diameter of the cavities 520*a*, 520*b*, 520*c*, 520*d*, 520*e*, 520*f*, 520*g*, 520*h* and the diameter of the protrusions 420*a*, 420*b*, 420*c*, 420*d*, 420*e*, 420*f*, 420*g*, 420*h* is less than 15% of the diameter of the protrusions 420*a*, 420*b*, 420*c*, 420*d*, 420*e*, 420*f*, 420*g*, 420*h*. In some implementations, the thickness or diameter of the protrusions 420*a*, 420*b*, 420*c*, 420*d*, 420*e*, 420*f*, 420*g*, 420*h* is such that the protrusions may freely move in the respective cavities 520*a*, 520*b*, 520*c*, 520*d*, 520*e*, 520*f*, 520*g*, 520*h* while remaining stable. In some implementations, a depth of the cavities 520*a*, 520*b*, 520*c*, 520*d*, 520*e*, 520*f*, 520*g*, 520*h* may be 10% or more than the length of the protrusions 420*a*, 420*b*, 420*c*, 420*d*, 420*e*, 420*f*, 420*g*, 420*h*.

In an example implementation, the cavities 520*a*, 520*b*, 520*c*, 520*d*, 520*e*, 520*f*, 520*g*, 520*h* have a depth of 8 mm and have a 3 mm diameter, and the protrusions 420*a*, 420*b*, 420*c*, 420*d*, 420*e*, 420*f*, 420*g*, 420*h* have a length of 6.5 mm and a diameter of 2.8 mm.

The dimensions provided herein are exemplary and are not intended to be limiting. Various dimensions may be utilized without departing from the scope of the disclosed subject matter. Moreover, the various cavities and protrusions may have dimensions different from one another, depending on, for example, the various sizes of the fingers 72, 74, 76, 78.

In some implementations, the fingers 72, 74, 76, 78 including the protrusions 420*a*, 420*b*, 420*c*, 420*d*, 420*e*, 420*f*, 420*g*, 420*h* may be formed of a hard, durable material, for example, a plastic. The chassis 400 may also be formed of a hard, durable material, for example, a metal. The material of the fingers 72, 74, 76, 78, and in particular the protrusions 420*a*, 420*b*, 420*c*, 420*d*, 420*e*, 420*f*, 420*g*, 420*h*, may be such that there is limited wear at the contact points 415 during use of the pumping mechanism 70. Additionally, the material of the protrusions 420*a*, 420*b*, 420*c*, 420*d*, 420*e*, 420*f*, 420*g*, 420*h* and the chassis 400 may be such that the materials do not negatively interact with or otherwise affect one another.

Implementations of the current subject matter provide a steadying and stabilizing force to the fingers 72, 74, 76, 78 with respect to the sidewalls 404 of the chassis 400 such that as the fingers 72, 74, 76, 78 move up and down within the recess 402, unwanted vibration and noise of the fingers 72, 74, 76, 78 are reduced or eliminated. Various alternatives of the disclosed implementations may be employed. For example, the protrusions 420*a*, 420*b*, 420*c*, 420*d*, 420*e*, 420*f*, 420*g*, 420*h* may be flexibly and/or retractably attached directly to the side regions 72*c,d*, 74*c,d*, 76*c,d*, 78*c,d* of the fingers 72, 74, 76, 78. Various other alternatives with respect to size and shape as discussed herein may also be employed without departing from the scope of the current subject matter.

Although the disclosure, including the figures, described herein may describe and/or exemplify these different variations separately, it should be understood that all or some, or components of them, may be combined.

Although various illustrative embodiments are described above, any of a number of changes may be made to various embodiments. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the claims.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. References to a structure or feature that is disposed "adjacent" another feature may have portions that overlap or underlie the adjacent feature.

Terminology used herein is for the purpose of describing particular embodiments only and is not intended to be limiting. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as, for example, "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" "or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, are possible.

In the descriptions above and in the claims, phrases such as, for example, "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A pumping mechanism, comprising:
a cam comprising a central axis;
a chassis comprising a recess within which the cam fits in a lengthwise extension along the central axis, wherein the recess comprises a first sidewall that defines an interior of the recess;

a plurality of fingers coupled to the cam and configured to move in a direction transverse to the central axis, wherein each of the plurality of fingers comprises a body and a protrusion comprising a distal end and a proximal end, wherein the protrusion extends from the distal end outward from a side region of the body in a direction transverse to the direction of movement of the plurality of fingers such that the proximal end is in direct surface contact with the first sidewall of the recess, and wherein the distal end of the protrusion is fitted within an elongated cavity formed in the side region of the body, wherein the elongated cavity has a proximal open end and a distal closed end, and wherein the distal end of the protrusion remains facing the distal closed end of the cavity during movement of the protrusion, wherein at least one of the plurality of fingers comprises a first protrusion and a second protrusion, wherein a proximal end of the first protrusion is in direct surface contact with the first sidewall of the recess, and a proximal end of the second protrusion is in direct surface contact with a second sidewall of the recess, the second sidewall being opposed to the first sidewall, wherein the first sidewall and the second sidewall are both straight; and
a spring fitted within the cavity, wherein the distal end of the protrusion contacts the spring.

2. The pumping mechanism of claim 1, wherein the distal end of the protrusion is removably fitted within the cavity.

3. The pumping mechanism of claim 1, wherein the proximal end of the protrusion comprises a rounded edge.

4. The pumping mechanism of claim 1, wherein at least one of the plurality of fingers comprise two protrusions, the two protrusions extending from opposing sides of the body of the at least one finger.

5. The pumping mechanism of claim 4, wherein the two protrusions are off-axis with respect to one another.

6. The pumping mechanism of claim 1, wherein the distal end of the protrusion is retractably connected to the side region of the body.

7. The pumping mechanism of claim 1, wherein the plurality of fingers comprises four fingers positioned in a linear arrangement along the central axis of the cam.

8. The pumping mechanism of claim 7, wherein the four fingers each comprise two protrusions, the two protrusions extending from opposing sides of the body of a corresponding finger of the four fingers.

9. A peristaltic infusion pump, comprising:
a tubing receiver configured to receive tubing for infusing a fluid; and
a pumping mechanism arranged to mechanically couple with the tubing and configured to act on at least a portion of the tubing to cause fluid flow through the tubing, the pumping mechanism comprising:
a cam comprising a central axis in line with the tubing;
a chassis comprising a recess within which the cam fits in a lengthwise extension along the central axis, wherein the recess comprises a first sidewall that defines an interior of the recess;
a plurality of fingers coupled to the cam and configured to move in a direction transverse to the central axis, wherein each of the plurality of fingers comprises a body and a protrusion comprising a distal end and a proximal end, wherein the protrusion extends from the distal end outward from a side region of the body in a direction transverse to the direction of movement of the plurality of fingers such that the proximal end is in direct surface contact with the first sidewall of the recess, wherein the distal end of the protrusion is fitted within an elongated cavity formed in the side region of the body, wherein the elongated cavity has a proximal open end and a distal closed end, and wherein the distal end of the protrusion remains facing the distal closed end of the cavity during movement of the protrusion, wherein at least one of the plurality of fingers comprises a first protrusion and a second protrusion, wherein a proximal end of the first protrusion is in direct surface contact with the first sidewall of the recess, and a proximal end of the second protrusion is in direct surface contact with a second sidewall of the recess, the second sidewall being opposed to the first sidewall, wherein the first sidewall and the second sidewall are both straight; and a spring fitted within the cavity, wherein the distal end of the protrusion contacts the spring.

10. The peristaltic infusion pump of claim 9, wherein the distal end of the protrusion is removably fitted within the cavity.

11. The peristaltic infusion pump of claim 9, wherein the proximal end of the protrusion comprises a rounded edge.

12. The peristaltic infusion pump of claim 9, wherein at least one of the plurality of fingers comprise two protrusions, the two protrusions extending from opposing sides of the body of the at least one finger.

13. The peristaltic infusion pump of claim 12, wherein the two protrusions are off-axis with respect to one another.

14. The peristaltic infusion pump of claim 9, wherein the distal end of the protrusion is retractably connected to the side region of the body.

15. The peristaltic infusion pump of claim 9, wherein the plurality of fingers comprises four fingers positioned in a linear arrangement along the central axis of the cam.

16. The peristaltic infusion pump of claim 15, wherein the four fingers each comprise two protrusions, the two protrusions extending from opposing sides of the body of a corresponding finger of the four fingers.

\* \* \* \* \*